(12) United States Patent
Majava

(10) Patent No.: US 12,036,010 B2
(45) Date of Patent: Jul. 16, 2024

(54) CARDIOGRAM MEASUREMENTS

(71) Applicant: Polar Electro Oy, Kempele (FI)

(72) Inventor: Ville Majava, Kempele (FI)

(73) Assignee: Polar Electro Oy, Kempele (FI)

( * ) Notice: Subject to any disclaimer, the term of this patent is extended or adjusted under 35 U.S.C. 154(b) by 1164 days.

(21) Appl. No.: 16/788,499

(22) Filed: Feb. 12, 2020

(65) Prior Publication Data

US 2020/0268266 A1 Aug. 27, 2020

(30) Foreign Application Priority Data

Feb. 26, 2019 (EP) .................................... 19159318

(51) Int. Cl.
*A61B 5/00* (2006.01)
*A61B 5/021* (2006.01)
(Continued)

(52) U.S. Cl.
CPC .......... *A61B 5/02438* (2013.01); *A61B 5/002* (2013.01); *A61B 5/02125* (2013.01); *A61B 5/02416* (2013.01); *A61B 5/1102* (2013.01); *A61B 5/4806* (2013.01); *A61B 5/681* (2013.01); *A61B 5/6844* (2013.01);
(Continued)

(58) Field of Classification Search
CPC . A61B 5/02438; A61B 5/002; A61B 5/02125; A61B 5/02416; A61B 5/1102; A61B 5/4806; A61B 5/681; A61B 5/6844; A61B 5/7285; A61B 5/05; A61B 2562/0257; H04B 17/104; A63B 24/0062; A63B 2220/89

See application file for complete search history.

(56) References Cited

U.S. PATENT DOCUMENTS 6,490,465 B1 * 12/2002 Mittelstadt ............ H04M 1/724
  343/702
2005/0264452 A1 * 12/2005 Fujishima ............ H01Q 9/0407
  343/700 MS (Continued)

FOREIGN PATENT DOCUMENTS

WO 2008/105837 A2 9/2008
WO 2009/142360 A1 11/2009

OTHER PUBLICATIONS

Extended European Search Report received for EP Patent Application No. 19159318.5, dated Aug. 8, 2019, 8 pages.

*Primary Examiner* — Angela M Hoffa
*Assistant Examiner* — Adam D. Kolkin
(74) *Attorney, Agent, or Firm* — FisherBroyles, LLP

(57) ABSTRACT

A solution for measuring a cardiogram of a user is disclosed. According to an aspect, a portable training computer includes a communication circuitry including a radio frequency antenna and configured to transmit a radio frequency signal through the antenna, a measurement circuitry coupled to the antenna and configured to measure an electric property of the antenna, and at least one processor configured to, in a first measurement mode, detect presence of an object in proximity with the antenna on the basis of the measured electric property, and in a second measurement mode, detect motion of a body of a user of the portable training computer with respect to the antenna on the basis of the measured electric property and compute a cardiogram of the user in the basis of the detected motion.

16 Claims, 6 Drawing Sheets

(51) Int. Cl.
*A61B 5/024* (2006.01)
*A61B 5/11* (2006.01)
*A63B 24/00* (2006.01)
*H04B 17/10* (2015.01)
*A61B 5/05* (2021.01)

(52) U.S. Cl.
CPC ........ *A61B 5/7285* (2013.01); *A63B 24/0062* (2013.01); *H04B 17/104* (2015.01); *A61B 5/05* (2013.01); *A61B 2562/0257* (2013.01); *A63B 2220/89* (2013.01)

(56) References Cited

U.S. PATENT DOCUMENTS

| | | | |
|---|---|---|---|
| 2008/0294019 A1* | 11/2008 | Tran | G16H 40/63 |
| | | | 600/301 |
| 2010/0305460 A1* | 12/2010 | Pinter | A61B 5/0507 |
| | | | 600/509 |
| 2010/0331715 A1* | 12/2010 | Addison | A61B 5/4818 |
| | | | 600/529 |
| 2013/0053653 A1* | 2/2013 | Cuddihy | A61B 5/0816 |
| | | | 600/301 |
| 2015/0109124 A1 | 4/2015 | He et al. | |
| 2016/0041531 A1 | 2/2016 | Mackie et al. | |
| 2016/0249857 A1* | 9/2016 | Choi | A61B 5/6898 |
| | | | 600/547 |
| 2016/0345845 A1* | 12/2016 | Ravid | A61B 5/02125 |
| 2017/0346178 A1* | 11/2017 | Shi | H04B 17/102 |
| 2019/0015041 A1* | 1/2019 | Chung | G16H 20/60 |

\* cited by examiner

CARDIOGRAM MEASUREMENTS

CROSS-REFERENCE TO RELATED APPLICATION

This application claims benefit and priority to European Application No. 19159318.5, filed Feb. 26, 2019, which is incorporated by reference herein in its entirety.

BACKGROUND

Field

The present invention relates to a field of physiological or biometric measurements and, in particular, to measuring a cardiogram of a user.

SUMMARY

A cardiogram may be measured by various sensors. A photoplethysmogram (PPG) sensor is an example of a cardiogram sensor. A PPG sensor conventionally comprises at least one light source, such as a light emitting diode (LED), and at least one photo sensor such as a photodiode. Light emitted by the LED(s) is directed to a skin of a user wearing the PPG sensor, and the light is delivered via the skin to the photodiode(s). An electrocardiogram (ECG) sensor is another type of heart activity sensor that is configured to measure electrical heart activity by using one or more electrodes attached to the user's skin. Ballistocardiogram (BCG) is another form of heart activity measure where ejections of blood into the great vessels of the user during each heart beat are detected. A ballistocardiographic scale is an example of a sensor measuring the BCG, wherein the user must stand on the scale to measure the BCG.

According to an aspect, there is provided a portable training computer comprising: a communication circuitry comprising a radio frequency antenna and configured to transmit a radio frequency signal through the antenna; a measurement circuitry coupled to the antenna and configured to measure an electric property of the antenna; and at least one processor configured to: in a first measurement mode, detect presence of an object in proximity with the antenna on the basis of the measured electric property, and in a second measurement mode on the basis the measured electric property, detect motion of a thorax of a user of the portable training computer with respect to the antenna and compute a cardiogram of the user on the basis of the detected motion, wherein the cardiogram represents the motion of the thorax, induced by the user's heart, with respect to the portable training computer.

In an embodiment, the at least one processor is configured to detect the proximity of the thorax with respect to the antenna in the first measurement mode and, upon detecting the proximity of the thorax with respect to the antenna, to trigger the second measurement mode.

In an embodiment, the at least one processor is configured to detect the proximity of the thorax with respect to the antenna in the first measurement mode and to trigger the second measurement mode during sleep time of the user.

In an embodiment, the portable training computer further comprises at least one motion sensor, wherein the at least one processor is configured to detect the proximity of the thorax with respect to the antenna in the first measurement mode on the basis of the electric property and motion measurement data, measured by the motion sensor, indicating a gesture where the portable training computer is brought to the proximity of the thorax.

In an embodiment, the portable training computer further comprises a photoplethysmogram, PPG, sensor, wherein the at least one processor is configured, in the second measurement mode, to detect a blood pulse wave from the cardiogram at a first time instant, to detect the same blood pulse wave in a PPG measured by the PPG sensor at a second time instant, and to compute a pulse transit time of the blood pulse wave on the basis of a difference between the first time instant and the second time instant.

In an embodiment, the at least one processor is configured to determine the first time instant from a detection time of the blood pulse wave offset by a non-zero-time offset factor.

In an embodiment, the PPG sensor is further configured to measure the PPG when not in the second measurement mode, and wherein the at least one processor is configured to trigger the second measurement mode and computation of the pulse transit time upon detecting a determined anomaly in the measured PPG.

In an embodiment, the communication circuitry comprises at least one further antenna configured to a different frequency band than said antenna, wherein the measurement circuitry is coupled to the at least one further antenna and configured to measure an electric property of the at least one further antenna, and wherein the at least one processor is further configured to compute the cardiogram in a third measurement mode on the basis of the measured electric property of the at least one further antenna.

In an embodiment, the at least one processor is configured, upon determining to enter the second measurement mode, to verify that a position of the antenna is suitable for the cardiogram measurements in the second measurement mode and, upon detecting that the position of the antenna is not suitable for the cardiogram measurements, carry out a function for correcting the position of the antenna.

In an embodiment, the portable training computer further comprises a user interface, wherein the function comprises outputting an instruction to a user to change the position of the portable training computer.

In an embodiment, the function comprises electrically modifying directivity of the antenna.

In an embodiment, the communication circuitry and the antenna are configured to comply with Bluetooth technology.

In an embodiment, the portable training computer is a wrist computer.

In an embodiment, the measurement circuitry is configured to measure the antenna impedance only when the communication circuitry is transmitting or receiving the radio frequency signal through the antenna.

In an embodiment, the communication circuitry is configured to transmit and receive data through the antenna.

In an embodiment, the portable training computer further comprises a memory configured to store one or more ranges of the electric property that indicate the proximity of the thorax and one or more, different ranges of the electric property that indicate the proximity of the finger or another object, and wherein the at least one processor is configured to distinguish, on the basis of the measured electric property and the stored ranges, whether there is the thorax or the finger or another object in the proximity with the antenna.

In an embodiment, the at least one processor is configured to trigger the second measurement mode upon distinguishing, on the basis of the measured electric property and the stored ranges, that the thorax is in the proximity with the antenna.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
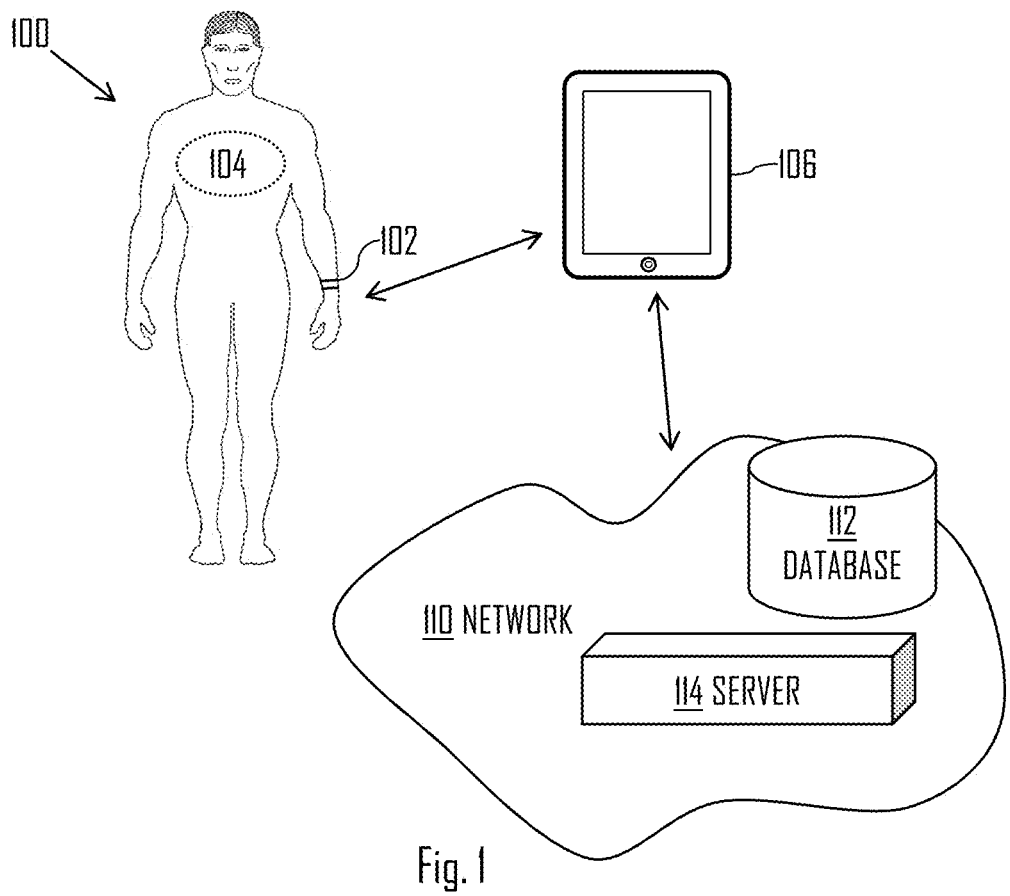
FIG. 1 illustrates a system to which embodiments of the invention may be applied.

FIG. 1 illustrates a system to which embodiments of the invention may be applied. Said system may be used to monitor cardiac activity of a user 100. A primary purpose for monitoring the cardiac activity may be monitoring physical training, activity, and/or inactivity of the user 100. The monitoring may be performed non-invasively. Embodiments described herein need not be limited to monitoring and/or measuring physical training of the user 100 and, thus, said system may be used to monitor physical activity and/or inactivity during the day and/or night (e.g. 24 hours a day) and/or on a need basis. Such may be possible by using one or more devices described with respect to FIG. 1 and in the embodiments below.

Referring to FIG. 1, the user 100 may wear a portable training computer that may be a wearable training computer, such as a wrist computer 102. In another example, the portable training computer may be and/or be wearable in another body part, e.g. in finger or in an apparatus such as a glove or a shirt. In some embodiments, the portable training computer is integrated as a part of the apparel. Due to simplicity reasons, let us now describe the portable training computer as being the wrist device 102. However, embodiments described in relation to wrist device 102 may be utilized by other types of portable training computers, i.e. the embodiments are not necessarily limited to wrist device or devices 102.

The wrist device 102 may be, for example, a smart watch, a smart device, sports watch, and/or an activity tracking apparatus (e.g. bracelet, arm band, wrist band). The wrist device 102 may be used to monitor physical activity of the user 100 by using data from internal sensor(s) comprised in the wrist device 102 data from external sensor device(s), and/or data from external services (e.g. training database 112). It may be possible to receive physical-activity-related information from a network 110, as the network may deliver, for example, physical activity-related information of the user 100. The network 110 may comprise the training database 112 and/or a server 114. The server 114 may be configured to enable data transfer between the training database 112 and some external device, such as the portable training computer. Hence, the database 112 may be used to store cardiac activity measurement data, for example.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN) and/or Near Field Communication (NFC), may also be used.

The wrist device 102 may comprise a heart activity sensor configured to determine cardiac activity of the user 100, such as heart rate, heart beat interval (HBI) and/or heart rate variability (HRV), for example. The heart activity sensor may comprise an optical cardiac activity sensor unit configured to measure the cardiac activity of the user 100 by using optical measurements. An example of such sensor is a PPG (photoplethysmography) sensor. The optical measurements may comprise light emitting diode(s) LED(s) of the PPG sensor emitting light towards body tissue of the user 100 and measuring bounced, reflected, diffracted, scattered and/or emitted light from the body tissue of the user 100 by using one or more photodiodes. The emitted light is modulated when travelling through veins of the user 100 and the modulation may be detected by the PPG sensor unit. By using detected optical measurement data, the wrist device 102 may determine cardiac activity of the user 100, such as the heart rate. The optical cardiac activity sensor unit may obtain via the measurement a measurement signal characterizing or carrying the cardiac activity information on the user. As understood, similar cardiac activity circuitry may be comprised in the other portable training computers described herein.

Figure 2:
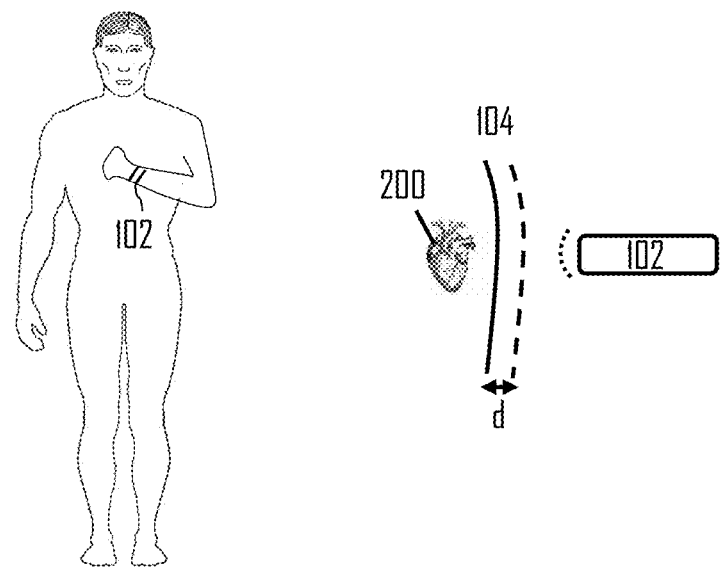
FIG. 2 illustrates a physiological phenomenon embodiments of the invention are configured to measure.

Let us now describe a physical phenomenon embodiments of the invention are configured to detect and monitor with reference to FIG. 2. As described in the Background, the ballistocardiogram (BCG) relates to monitoring mechanical movement of the heart that can be recorded by a suitable sensor. Conventional solutions for measuring the BCG include motion sensors and pressure sensors that require physical contact with the user. As illustrated in FIG. 2, the heart 200 ejects blood into the great arteries in each heartbeat. The ejection causes expansion of the arteries that result in minor extension of the thorax 104 of the user 100 as well. In other words, mechanical back-and-forth motion is induced into the thorax by the heartbeats. In the embodiments described below, the portable training computer comprises a wireless sensor configured to measure the BCG wirelessly without a need for mechanical or physical coupling to the user's body. As illustrated in FIG. 2, when the portable training computer 102 is the wrist computer, the user may bring the wrist computer to the proximity of the thorax to measure the BCG wirelessly.

Figure 3:
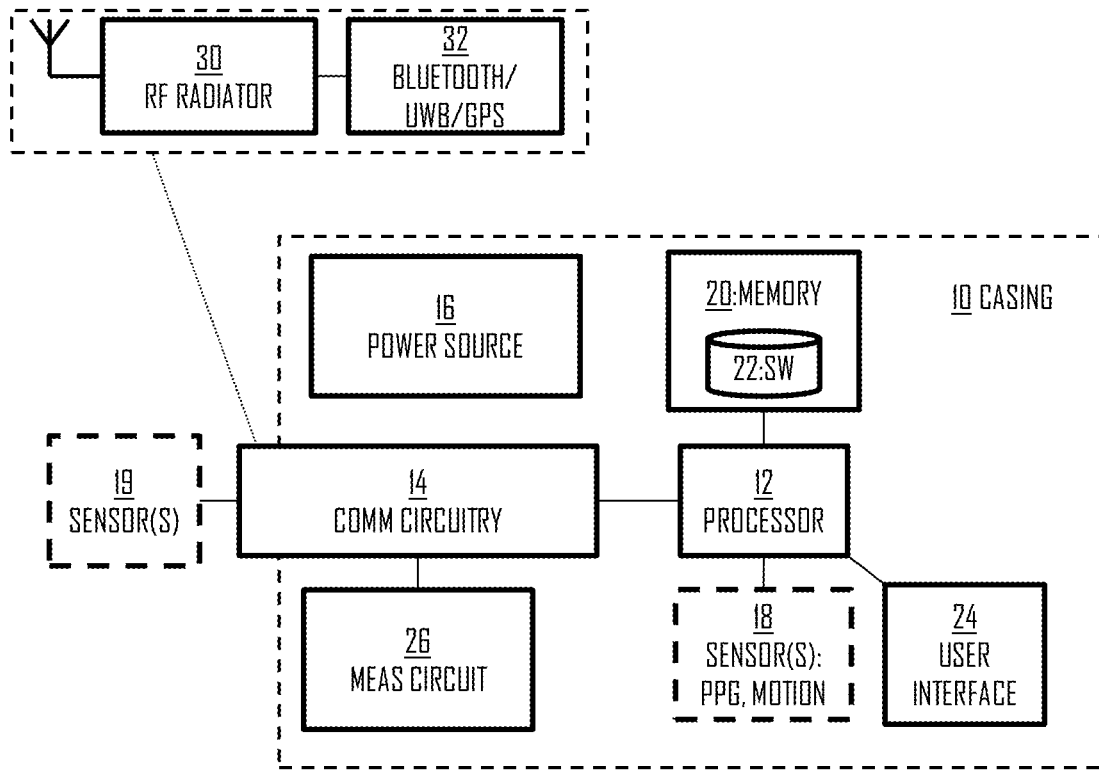
FIG. 3 illustrates a block diagram of a portable training computer according to an embodiment of the invention.

Referring to FIG. 3, let us now describe the portable training computer according to an embodiment of the invention. The portable training computer comprises a communication circuitry 14 comprising a radio frequency antenna 30 and configured to transmit a radio frequency signal through the antenna 30; a measurement circuitry 26 coupled to the antenna 30 and configured to measure an electric property of the antenna 30; and at least one processor 12 configured to detect, in a first measurement mode, presence of an object in proximity with the antenna 30 on the basis of the measured electric property and, in a second measurement mode, to detect motion of the user's body with respect to the antenna on the basis of the measured electric property and to compute a cardiogram of the user in the basis of the detected motion. The cardiogram may be understood to be a ballistocardiogram (BCG) measured wirelessly on the basis of the measured electric property. From another perspective, the cardiogram may be understood to be an electromagnetic cardiogram (EMCG) because the sensor (antenna) detects electromagnetic phenomena created by the heart through electromagnetic sensing, e.g. the change in antenna impedance or resonance frequency. The electromagnetic phenomena may include not only the physical motion of the user's body that affects the antenna properties, as described above, but also change in electromagnetic characteristics in the body tissue caused by the heartbeat, e.g. a change in magnetic susceptibility of the body tissue. Other potential electromagnetic characteristics include permittivity, conductance, permeability, and electrical susceptibility of the body tissue. Such electromagnetic characteristics may also affect the electric property of the antenna.

In an embodiment, the user's heart rate may be computed from the cardiogram, e.g. the BCG or EMCG. The cardiogram has a sinusoidal component that represents the heart rate.

In an embodiment, the user's respiratory rate is computed from the cardiogram. The cardiogram has another sinusoidal component that represents the respiratory rate. The heart rate may be distinguished from the respiratory rate in the measured cardiogram signal by using proper signal filtering.

In an embodiment, the first measurement mode is a proximity detection mode where the processor determines whether or not the object is within the proximity of the antenna. An output of the determination in the proximity detection mode may be binary, e.g. 'yes' or 'no'.

In an embodiment, the second measurement mode is the cardiogram measurement mode in which the processor processes the cardiogram from the measured electric property. The processing may comprise filtering the measured electric property, e.g. averaging samples of the measured electric property over a determined averaging window.

In an embodiment, the portable training computer further comprises the ECG sensor for measuring the ECG. The ECG may be used as a reference for detecting the blood pulse wave and as an input for processing the cardiogram, e.g. the BCG or EMCG. For example, the cardiogram measured wirelessly may be transformed into a frequency domain by a Fourier transform and, thereafter, filtered by using a filter, and the filter parameters may be selected by using the ECG, e.g. the heart rate measured from the ECG.

The portable training computer may comprise a casing 10 and a fixing mechanism configured to attach said casing 10 to an object such as the user 100. The fixing mechanism may be a wrist strap in a case where the portable training computer is the wrist computer. The fixing mechanism may be the apparel to which the portable training computer may be integrated or removably attached. The casing may house at least some of the electronic circuits of the portable training computer. The casing may further store a power source 16 of the portable training computer, e.g. a battery.

The communication circuitry 14 may provide the portable training computer with capability of transmitting and receiving signals and data wirelessly. The communication circuitry 14 may comprise a radio modem 32 configured to operate according to one or more radio communication protocols such as Bluetooth® technology developed within Bluetooth Special Interest Group (SIG). The supported Bluetooth technology may include Bluetooth Smart®, Bluetooth Low energy (BTLE) or, in general, any one or more of the Bluetooth evolution versions from version 1.0 up to 5.0 and beyond in the future. In another embodiment, the radio modem supports another communication technology such as a global navigation satellite system (GNSS) technology such as the Global Positioning System or Galileo. In another embodiment, the radio modem 32 supports ultra-wideband (UWB) technology. In an embodiment, the portable training computer comprises multiple radio modems supporting different radio communication protocols and operating on different frequency bands.

The antenna may be comprised in a radio frequency (RF) radiator circuitry coupled to the radio modem 32 and configured to receive transmission signals from the radio modem 32 and to radiate the transmission signals as transmission bursts. In other embodiments such as the GNSS, the RF radiator circuitry may be configured to receive only.

The casing 10 may house the measurement circuitry 26 coupled to the antenna and configured to measure an electric property of the antenna for determining the proximity of an object with respect to the antenna on the basis of the measured electric property. The measurement circuitry 26 may, together with the antenna, form an RF touch-sensitive circuit. The measured electric property may be any one of impedance, resonance frequency, and standing wave ratio of the antenna. The object in the proximity causes a disturbance in near-field characteristics of the antenna, and the disturbance can be measured from at least these electric properties of the antenna. The disturbance may differ depending on the position of the object with respect to the antenna and, as a consequence, the position of the object with respect to the antenna can be measured from the electric property. This enables detecting the motion of the thorax with respect to the portable training, as describe above in connection with FIG. 2. It may, however, be used for other purposes such as user interfacing.

In an embodiment, the measurement circuitry 26 may be configured to measure the antenna whenever the antenna is emitting and/or absorbing radio energy. With the transmission bursts, emission and/or absorption of RF energy by the antenna may be considered.

The apparatus may comprise a bezel in which at least a part of the RF radiator circuitry 30 is integrated. For example, the bezel may serve as the antenna of the RF radiator circuitry 30. The bezel may be attached to the casing 10 in a fixed or rotatable manner. Because a portion of the circuitry 14 may be external to the casing 10, e.g. the antenna 30, the communication circuitry is illustrated in FIG. 3 to be partly external to the casing 10.

The radio modem 32 may provide the portable training computer with capability of communicating with external sensors 19, for example. An example of such a system would comprise a heart activity transmitter comprised in a chest strap and the apparatus as a wrist computer. Another example of such a system would comprise a pedaling sensor comprised in a pedal of a bicycle and the apparatus as a bike computer attached to a handlebar of the bicycle. In another embodiment, the radio modem may provide a communication connection with another computer device such as a mobile phone, a tablet computer, or a server computer.

The portable training computer may further comprise a user interface 24 comprising a display screen and input means such as buttons or a touch-sensitive display. In an embodiment, the antenna and the measurement circuitry 26 provides the RF-touch-sensing as a user input system. Additionally, the at least one processor 12 may output information regarding a measured exercise to the user interface 24 for display to the user.

The apparatus may further comprise at least one internal sensor 18 in the casing 10. For example, the at least one internal sensor 18 may comprise an electrocardiogram ECG sensor or a photoplehysmogram (PPG) sensor for measuring the heart activity. Additionally, one or more motion sensors may be comprised in the casing 10. The motion sensor may include one or more accelerometers, a gyroscope, and/or a magnetometer. In an embodiment, the processor may use the at least one motion sensor to for performing motion compensation on the measured electrical property of the antenna. The motion compensation is performed to negate the effect of the motion of the portable training computer when measuring the electrical property. The motion may be caused by a shaky hand, for example.

The at least one processor 12 may further comprise or have access to at least one memory 20 comprised in the casing 10. The memory 20 may store a computer program code 22 comprising instructions readable and executable by the at least one processor 12 and configuring the operation of the at least one processor 12. In an embodiment, at least some features of the measurement circuitry 26 are defined by software and, for that purpose, the at least one memory 20 may be accessible to it as well.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), graphics processing units (GPUs), processors, controllers, micro-controllers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Figure 4:
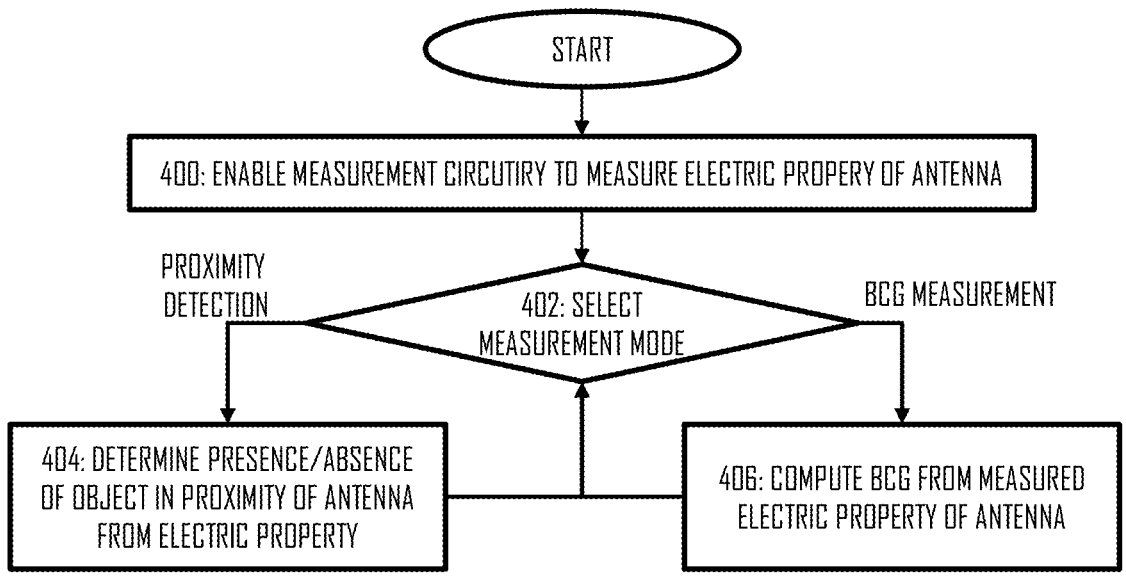
FIG. 4 illustrates a flow diagram of a process for a portable training computer using proximity measurements for multiple purposes.

As described above, the antenna may be used for three purposes: to transmit and/or receive data wirelessly, to detect proximity of the object, and to measure the cardiogram, e.g. the BCG or EMCG. FIG. 4 illustrates an embodiment of a process for configuring the at least one processor 12 accordingly. Referring to FIG. 4, the process comprises as performed by the least one processor 12: enabling the measurement circuitry 26 to measure the electric property of the antenna (block 400); selecting a measurement mode (block 402) between at least the proximity detection mode and the cardiogram measurement mode; upon selecting the proximity detection mode, determining presence/absence of the object within the proximity of the antenna form the measured electric property of the antenna (block 404); upon selecting the cardiogram measurement mode, computing the cardiogram from the measured electric property of the antenna (block 406). From blocks 404 and 406, the process may return to block 402 for changing the measurement mode.

In an embodiment of block 404 where the proximity detection is based on the antenna impedance, the memory 20 may store at least one range of impedance values that defines the proximity of the object. If the measured impedance of the antenna falls within the at least one range, the processor may determine that the object is within the proximity of the antenna. A similar procedure may be applied to the other electric properties, e.g. the resonance frequency and the standing wave ratio of the antenna.

Figure 5:
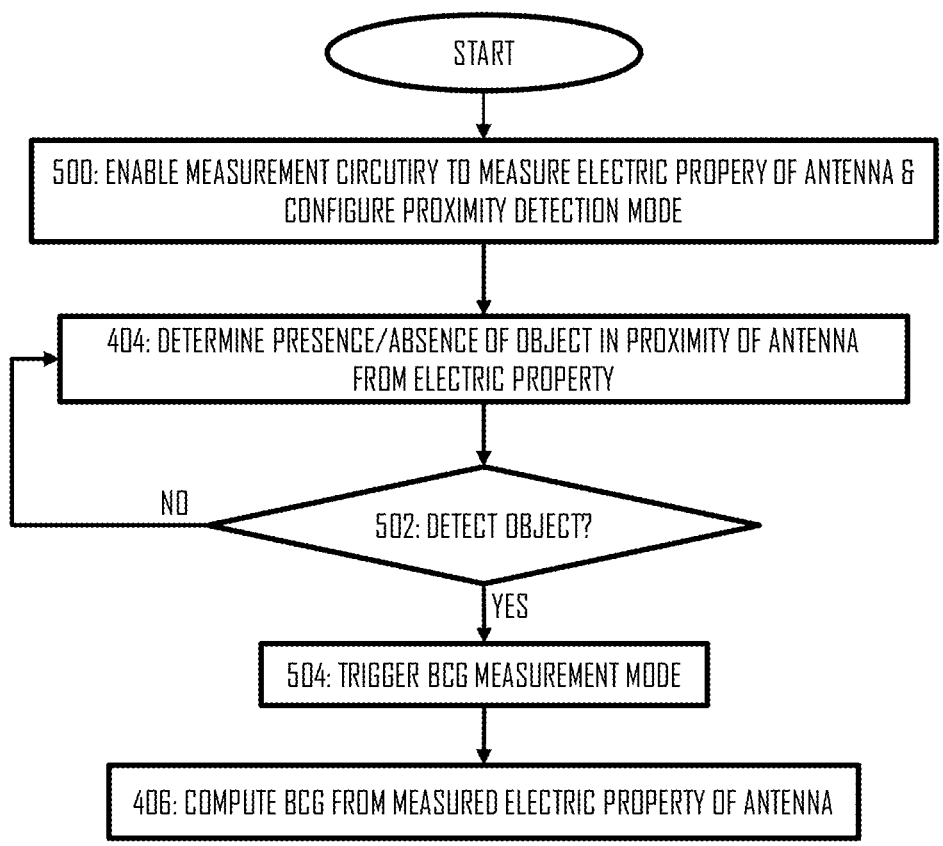
FIG. 5 illustrates a process for triggering a cardiogram measurement mode as a response to proximity detection according to an embodiment of the invention.

In an embodiment, triggering the cardiogram measurement mode is responsive to the proximity detection in the proximity detection mode. The processor may be configured to detect the proximity of the user's thorax within the proximity of the antenna and, as a response, trigger the cardiogram measurement mode. FIG. 5 illustrates such an embodiment. Referring to FIG. 5, the processor enables the measurement circuitry 26 to measure the electric property of the antenna and triggers the proximity detection mode in block 500. Thereafter, the processor performs the proximity detection on the basis of the measured electric property received from the measurement circuitry 26 in block 404. In block 502, it is determined whether or not the measured electric property indicates that the object is within the proximity of the antenna. If no detection of the object can be made, the process may return to block 404. If the object is detected, the process proceeds to block 504 in which the BCG measurement mode is triggered. Thereafter, the processor may start measuring the cardiogram from the electric property.

The proximity of the thorax may induce a different change to the electric property of the antenna than a finger, for example. The memory may store one or more ranges of the electric parameter that indicate the proximity of the thorax and one or more, different ranges of the electric parameter that indicate the proximity of the finger or another object.

In an embodiment, the processor uses the process of FIG. 5 to trigger the BCG measurement mode when performing sleep analysis for the user during the user's sleep time. The sleep time is an advantageous time for measuring the blood pressure because external stress factors have reduced effect on the blood pressure. The process of FIG. 5 may thus be triggered upon the processor 12 detects that the user is sleeping. The proximity detection mode may be used to detect when the user brings the portable training computer to the proximity of the thorax for the cardiogram measurements.

Figure 6:
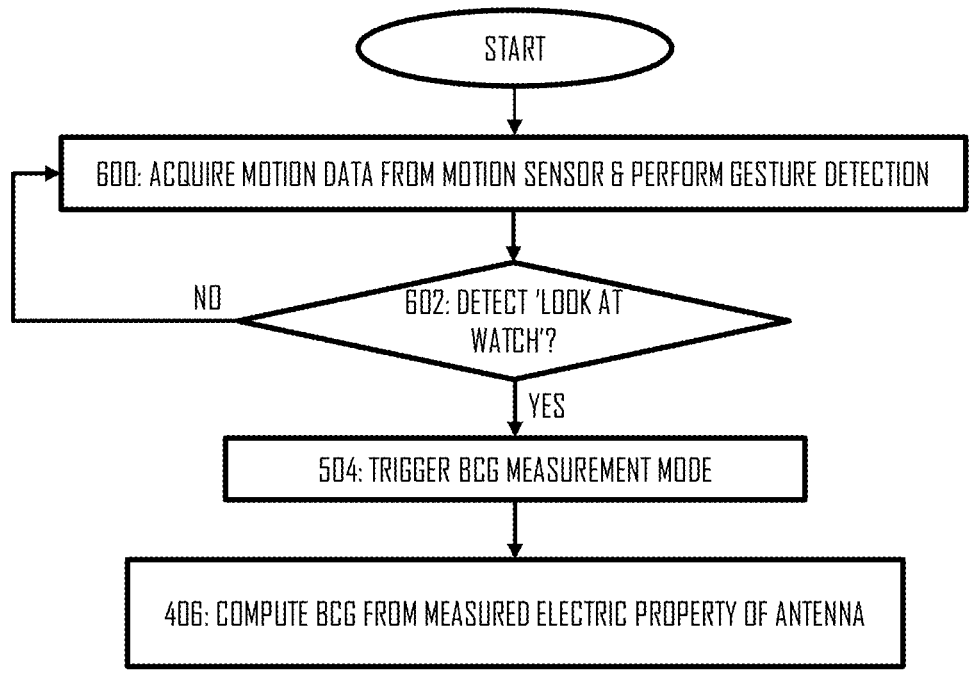
FIG. 6 illustrates a process for triggering a cardiogram measurement mode as a response to gesture detection according to an embodiment of the invention.

FIG. 6 illustrates another embodiment for detecting the presence of the thorax. In the embodiment of FIG. 6, the motion sensor(s) are used for detecting a gesture that indicates the presence of the thorax in the proximity of the antenna. When the wearable training computer is the wrist computer, the gesture may be 'look at watch' gesture where the user brings the wrist towards the chest to look at the watch face, as illustrated on the left hand side of FIG. 2. The motion sensors used for detecting this gesture may include the accelerometers and the gyroscope.

Referring to FIG. 6, the processor enables the motion sensors to measure the user's motion and acquires motion data from the motion sensors in block 600. The processor further performs gesture detection on the motion data. The gesture detection may be based on learned reference trajectories against which the motion data is compared. If sufficient correlation is discovered between the motion data and a reference trajectory, a gesture associated with the reference trajectory may be detected. In block 602, it is determined whether or not the motion data has sufficient correlation with a reference trajectory associated with the 'look at watch' gesture. If not, the process returns to block 600. If the correlation is discovered, the process proceeds to block 504 where the cardiogram measurement mode is triggered. Block 504 may in this embodiment comprise enabling the measurement circuitry 26 to measure the antenna impedance. In the cardiogram measurement mode, the electric property of the antenna received from the measurement circuitry is processed into the cardiogram data by the processor.

In an embodiment, the processor combines the embodiments of FIGS. 5 and 6. For example, upon detecting the 'look at watch' gesture', the processor may enable the measurement circuitry 26 to measure the antenna impedance (block 500). Upon detecting the object/thorax within the proximity of the antenna, the BCG measurement mode may be triggered (block 504 in FIG. 5).

In an embodiment the cardiogram measured according to the embodiments described herein is used for measuring a pulse transit (PTT) time representing velocity of a blood pulse in the user's arteries. The blood pulse is modulated on its way through the human body. The modulation may be caused by various physiological conditions and functions. Therefore, characteristics of the blood pulse wave may comprise representation of such physiological conditions. One set of such characteristics may include propagation characteristics of the blood pulse wave. The propagation characteristics may be considered as time characteristics that represent the PTT, for example, within a certain distance in the human arteries. Equivalent characteristics may include pulse propagation velocity which is proportional to the PTT. The PTT may be utilized for estimating blood pressure, clogging of arteries, or other medical conditions in a non-invasive manner.

Figure 7:
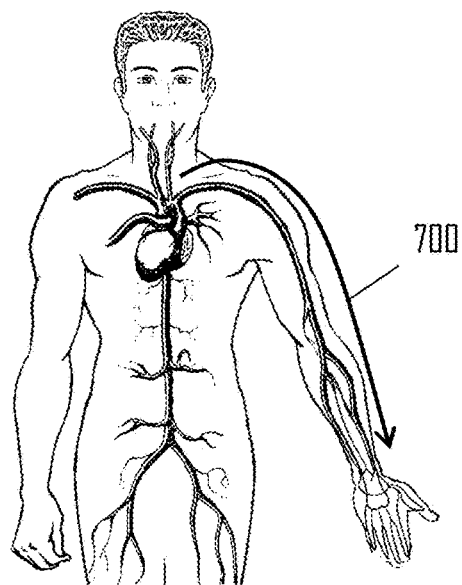
FIG. 7 illustrates a pulse transit time in a human body.

The cardiogram may be used to detect the blood pulse wave in the thorax area, and the portable training computer may have a further cardiac sensor for detecting the blood pulse wave at another location on the user's body. For example, when the portable training computer is the wrist computer, the wrist computer may comprise a PPG sensor for detecting the blood pulse wave from the user's wrist area. As illustrated in FIG. 7 by numeral 700, the PTT would then represent a propagation time of the blood pulse wave from the thorax area to the wrist area.

Figure 8:
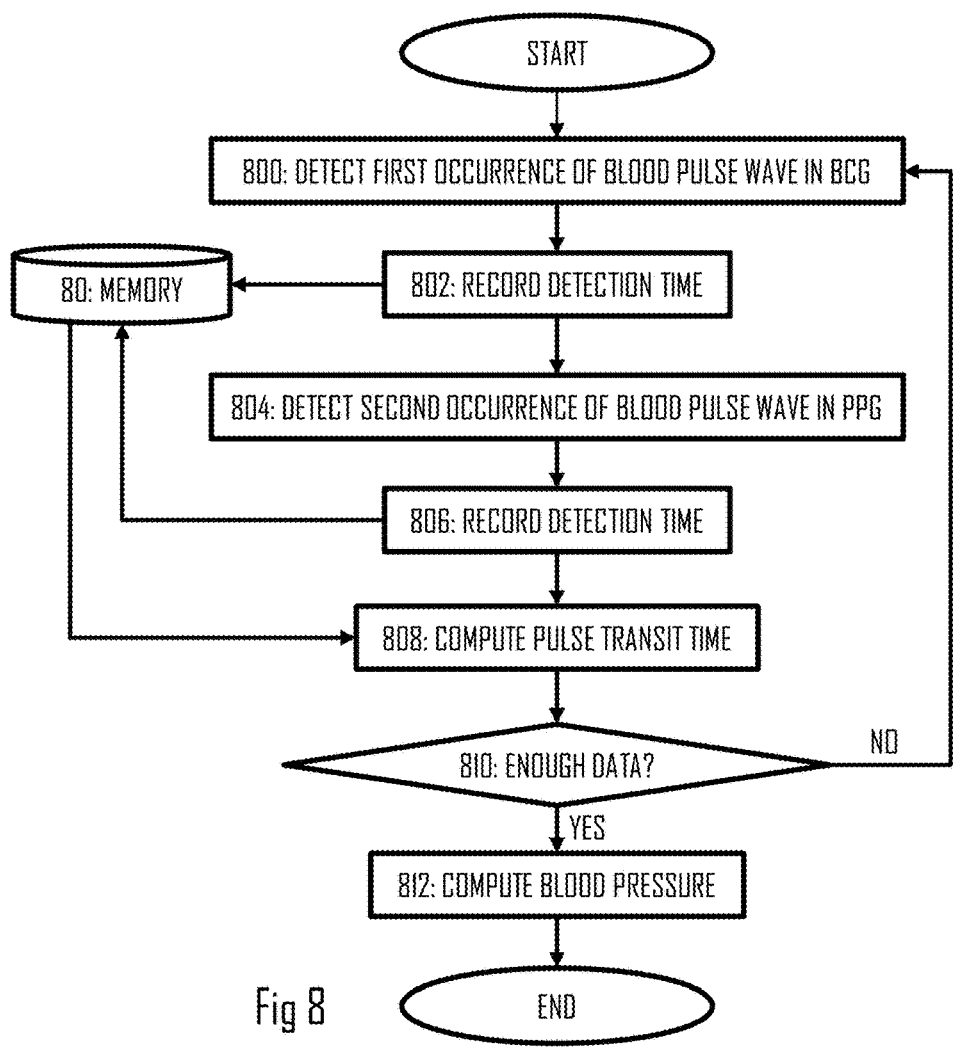
FIG. 8 illustrates a flow diagram of a process for measuring blood pressure by using cardiogram according to an embodiment of the invention.

FIG. 8 illustrates an embodiment of a process, executed by the at least one processor, for computing the blood pressure by using the cardiogram measured according to any one of the embodiments described herein. The process of FIG. 8 may be executed in the cardiogram measurement mode or at least by using measurement data acquired in the cardiogram measurement mode. Referring to FIG. 8, the process comprises detecting a first occurrence of a blood pulse wave in a cardiogram signal (block 800). The first occurrence may be detected by using a peak detecting for the cardiogram signal. The blood pulse ejected by the heart brings the thorax closer to the portable training computer, thus allowing the detection of the ejection from closer proximity of the thorax. Block 802 may comprise recording the detection time of the first occurrence as a first time instant in a memory 80.

In an embodiment, block 802 comprises determining the first time instant from the detection time of the blood pulse wave as offset by a non-zero time offset factor. The offset factor may compensate for the delay between the time of ejection of the blood pulse wave by the heart and the disposition of the thorax. The offset factor may be about 10 microseconds, for example. The offset factor may depend on the user characteristics and it may be determined when calibrating the PTT measurements.

In block 804, the processor detects a second occurrence of the blood pulse wave, this time in the PPG signal. The detection time may also be stored in the memory as a second time instant in block 806. Upon detecting the blood pulse wave two times, the pulse transit time may be computed in block 808 on the basis of the difference between the first time instant and the second time instant. The PPG sensing and the cardiogram sensing may be synchronized to a common clock and, thus, the first time instant and the second time instant are synchronized as well.

In block 810, it may be determined whether or not sufficient amount of PTT data is available for blood pressure estimation. Typically, a single PTT value may not be statistically sufficient. Upon detecting that further PTT data may be acquired and the process returns to block 800. Upon having the sufficient amount of PTT data, the blood pressure is computed in block 812. The blood pressure is inversely proportional to the PTT, and a mean blood pressure (MBP) may be computed according to the following Equation:

$$MBP \approx \frac{D}{K\,PTT} - \frac{M}{K}$$

Note that the ratios D/K and M/K can be estimated as single parameters during calibration of the blood pressure estimation, thus allowing us to avoid a distance D to be estimated separately. The distance D represents the distance from the heart to the location of the PPG sensor head. As a result, we have a direct correspondence between the MBP and the PTT and we can determine the MBP by measuring the PTT.

As described above, the blood pulse wave may carry information on various physiological conditions. The PTT may represent, for example, the user's 10 stress level. As a consequence, the process of FIG. 8 may be modified to estimate a physiological condition other than the blood pressure. Block 812 may thus comprise mapping the measured PPT to an indicator of the other physiological condition. The mapping may comprise further inputs such as a heart rate and/or a heart rate variability (variation of consecutive R wave intervals (R-R intervals) of blood pulse waves, and/or a breathing pattern that may be detected through ECG or PPG measurements. In the ECG, the breathing pattern may show in an amplitude component and a phase component of the ECG measurement signal, and the PPG measurement signal may similarly indicate the breathing pattern. Furthermore, the BCG computed according to any one of the embodiments described herein may be used to indicate the breathing pattern. In addition to the stress level, the PTT may be used as an indicator of a quality of sleep, aging, fitness level, health state, fatigue estimation (psychological, emotional and physiological), recovery estimation, presence of a sickness such as diabetes, or as an indicator of the user having a habit of smoking. For example, it is known that the blood pressure fluctuations (especially the in the systolic blood pressure) are a function of the mind state of the person and, thus, the PTT is also an indirect measure of this. An embodiment uses the PTT as an input to a stress relieve system such as through a neuro-cardio biofeedback loop incorporating heart rate variability and cardiac coherence, as used in many neuro-rehabilitation devices. Another example is the finer analysis of sleep patterns using the PTT. Indeed, sleep patterns are driven by an oscillation between wake and deep sleep passing through state of dreams. The PTT as a correlate to mind states will thus fluctuate according to the sleep state of the person. Thus variability in the PTT may be considered, as an indicator of the physiological condition of sleep state, e.g. disturbed sleep and associated potentially poorer quality of sleep.

Figure 9:
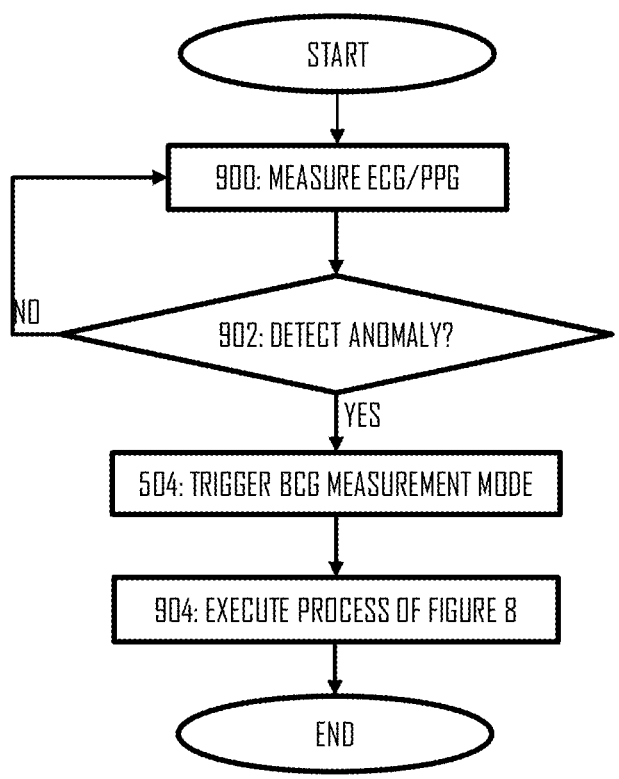
FIG. 9 illustrates a process for triggering ad hoc cardiogram measurements according to an embodiment of the invention.

In an embodiment, the cardiogram measurement mode is triggered upon detecting an anomaly in a measurement signal measured from the user 10. FIG. 9 illustrates an embodiment for triggering the cardiogram measurement mode upon detecting an anomaly in a monitored ECG or PPG signal. The anomaly may be, for example, an irregular heartbeat, heart fibrillation, etc. Accordingly, the ECG/PPG sensor may be configured to measure the ECG/PPG when not in the cardiogram measurement mode, and the at least one processor may be configured to trigger the cardiogram measurement mode and computation of the PTT upon detecting the anomaly in the measured ECG/PPG.

Referring to FIG. 9, the process comprises measuring the ECG/PPG (block 900). The processor may analyse the ECG/PPG and, upon detecting the anomaly in the ECG/PPG (YES in block 902), trigger the cardiogram measurement mode in block 504 and execute the process of FIG. 8 or an embodiment thereof (block 904) to perform further analysis of the user 10. In the embodiment of FIGS. 8 and 9, the positioning of the portable training computer with respect to the thorax may be verified before triggering the cardiogram measurements, as described in the embodiments above and below.

As described above in connection with FIG. 3, the portable training computer may comprise multiple radio modems and respective antennas tuned to different radio frequencies. As known in the art of radio communications, radio signals on different frequencies have different penetration capabilities. A radio signal on a lower frequency band penetrates deeper than a radio signal on a higher frequency band. This characteristic may be utilized in the cardiogram measurements. In an embodiment, the communication circuitry comprises multiple antennas tuned to different frequencies, and the measurement circuitry is coupled to the antennas and configured to measure electric properties of the antennas. The at least one processor may employ multiple cardiogram measurements modes, one cardiogram measurement mode using one of the antennas and another cardiogram measurement mode using another one of the antennas. For example, the Bluetooth or GNSS antenna may be used for measuring the proximity and motion of the thorax with respect to the Bluetooth/GNSS antenna, while the UWB antenna tuned to lower frequencies capable of penetrating deeper into the user's tissue may be used for measuring the motion of the heart itself directly.

Figure 10:
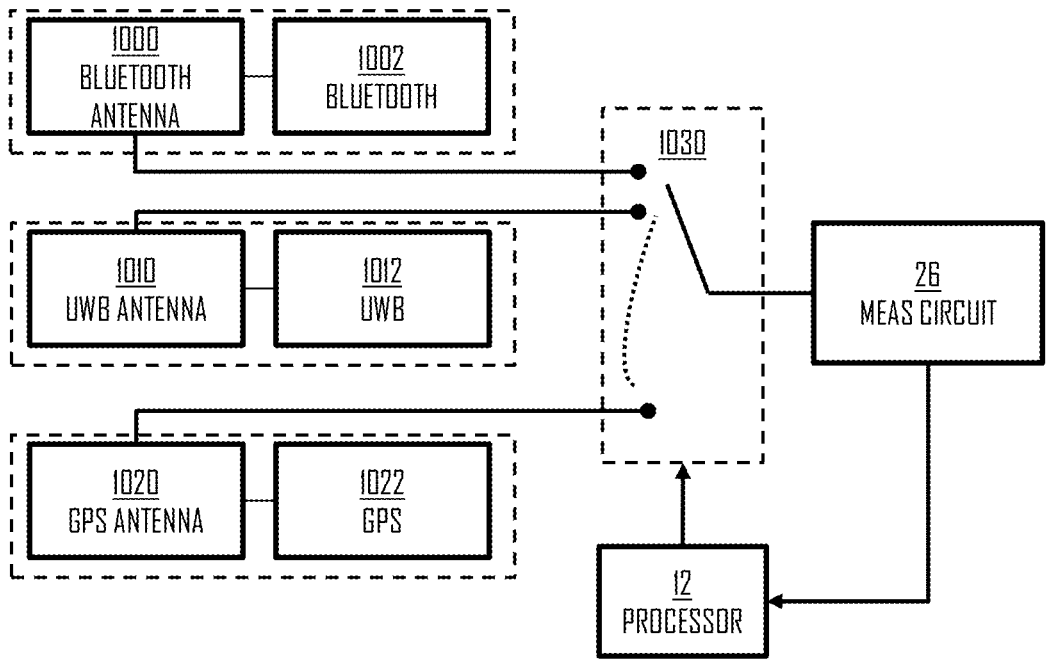
FIG. 10 illustrates a structure for using multiple antennas for measuring the cardiogram according to an embodiment of the invention.
Figure 11:
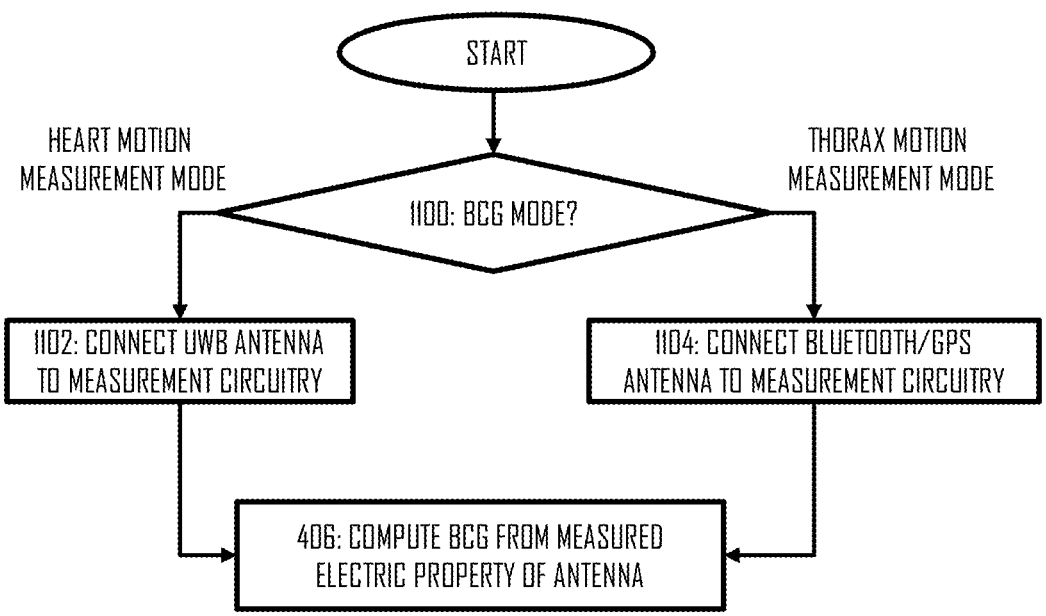
FIG. 11 illustrates an embodiment for selecting an antenna for a cardiogram measurement mode.

FIG. 10 illustrates a block diagram of an embodiment of the portable training computer according to such an embodiment. In the embodiment of FIG. 10, a Bluetooth® communication circuitry may comprise a Bluetooth antenna 1000 and a Bluetooth radio modem 1002, an UWB communication circuitry may comprise an UWB antenna 1010 and an UWB radio modem 1012, and a GNSS communication circuitry may comprise a GPS antenna 1020 and a GPS radio modem 1022. The antennas 1000, 1010, 1020 may be electrically coupled to a switch 1030 configured to couple one (or more) of the antennas 1000, 1010, 1020 to the measurement circuitry 26, according to the measurement mode selected by the processor 12. The processor 12 may thus, upon selecting a measurement mode, configure the switch 1030 to connect one or more of the antennas to the measurement circuitry 26 for the measurement of the electric property from the selected antenna(s). FIG. 11 illustrates a process for controlling the switch 1030 as performed by the processor 12.

Referring to FIG. 11, the processor may support multiple cardiogram measurement modes and select the BCG measurement mode in block 1100. Upon selecting the thorax motion measurement mode, the process may proceed to block 1104 where an antenna on a high frequency band is selected, e.g. the Bluetooth or GNSS antenna, and the respective antenna is connected to the measurement circuitry 26. The high frequency band may refer to a frequency band above 1 Gigahertz (GHz). Upon selecting the heart motion measurement mode, the process may proceed to block 1102 where an antenna on a low frequency band is selected and the respective antenna is connected to the measurement circuitry 26. The low frequency band may refer to a frequency band below 1 Gigahertz (GHz).

Upon selecting the cardiogram measurement mode, the measurement circuitry measures the electric property from the respective antenna, and the processor executes block 406 to compute the cardiogram.

In some embodiments described above, the processor may trigger the BCG measurement mode autonomously, e.g. upon detecting the gesture or proximity of the thorax. In another embodiment, the processor triggers the cardiogram measurement mode as a response to a user input through the user interface. The user may thus initiate the cardiogram measurement mode by controlling the processor to enter the cardiogram measurement mode. This may be preceded by the processor proposing the cardiogram measurement mode to the user, e.g. by proposing a blood pressure measurement in a regular manner (every morning, for example).

Figure 12:
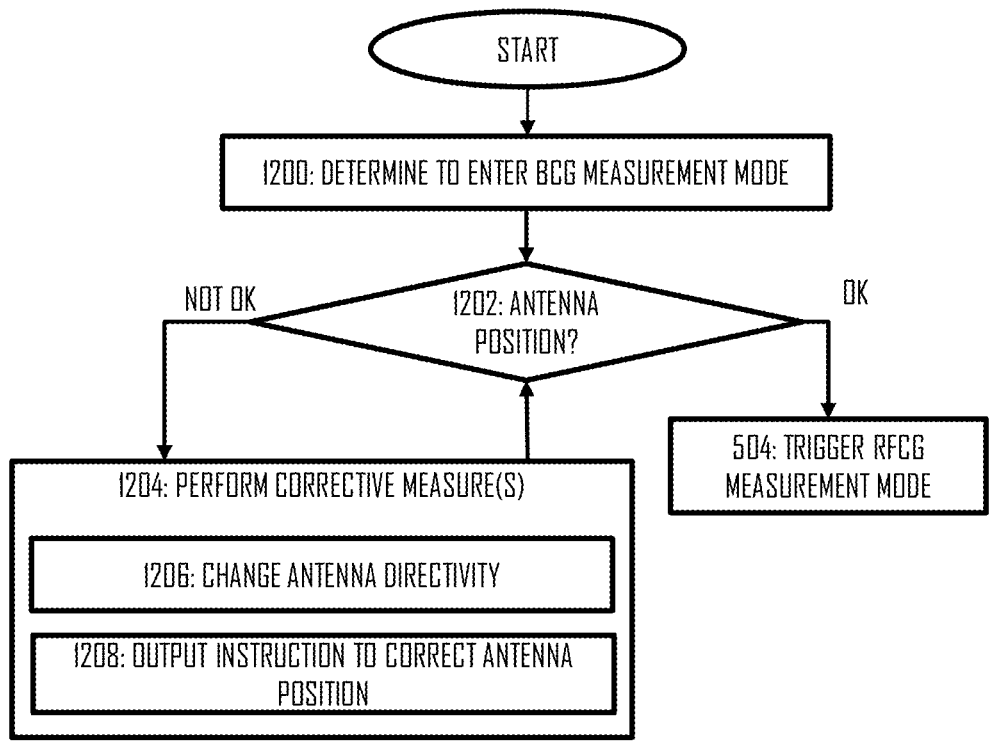
FIG. 12 illustrates an embodiment for verifying antenna positioning for the cardiogram measurement mode.

FIG. 12 illustrates an embodiment for the processor to control the alignment of the antenna to a position suitable for the cardiogram measurements. Referring to FIG. 12, the processor may determine to enter the cardiogram measurement mode in block 1200. Block 1200 may be executed as a response to the user input instructing the cardiogram measurements, detecting that the user's sleep time has begun, or through another criterion. Upon determining to enter the cardiogram measurement mode, the processor may check the antenna position (block 1202), e.g. as a part of the process of FIG. 5 or as an independent process. Block 1202 may comprise analysing the position of the antenna with respect to the thorax by using gyroscope measurement data and/or the proximity measurement mode. Upon detecting that the antenna is in a suitable position for the cardiogram measurements, the process proceeds to block 504 where the cardiogram measurement mode is triggered. Upon detecting that the antenna position is not suitable for the cardiogram measurements, the processor may trigger a corrective measure for changing the positioning of the antenna with respect to the user's thorax (block 1204). In an embodiment, such a measure comprises instructing the user to correct the alignment of the portable training computer (block 1208). The instruction may further direct the user to change the position of the portable training computer to a desired direction.

In an embodiment where the antenna comprises an antenna array, the corrective measure may comprise changing the directivity of the antenna (block 1206). The antenna array enables beamforming radiation in which radio lobes can be adjusted in a spatial domain. By inducing desired phase differences to radio signals radiated from the different antennas of the antenna array, destructive interference of the radio signals may be created towards undesired directions. In a similar manner, the radio energy may be focused to a desired direction or directions by the appropriate phasing of the radio signals. Such a controlled directivity applies to both transmission and reception. Block 1206 may thus comprise changing a beamforming configuration of the antenna array by changing phase shifts associated with the antennas of the antenna array. The phase shifting may be realized in a digital and/or analogue domain. The changes in block 1206 may be carried out in an opportunistic manner, e.g. the processor may change the beamforming configuration in block 1206 and return to block 1202 to check whether the change resulted in the suitable positioning of the antenna.

It will be obvious to a person skilled in the art that, as the technology advances, the inventive concept can be implemented in various ways. The invention and its embodiments are not limited to the examples described above but may vary within the scope of the claims.

The invention claimed is:

1. A portable training computer comprising:
a communication circuitry comprising a radio frequency antenna and configured to transmit a radio frequency signal through the antenna;
a measurement circuitry coupled to the antenna and configured to measure an electric property of the antenna, wherein the measured electric property of the antenna comprises at least one of an impedance, a resonance frequency, and a standing wave ratio of the antenna; and
at least one processor configured to,
in a first measurement mode, detect proximity of the thorax with respect to the antenna on the basis of the measured electric property, and upon detecting the proximity of the thorax with respect to the antenna, to trigger a second measurement mode, and
in the second measurement mode on the basis of the measured electric property, detect motion of a thorax of a user of the portable training computer with respect to the antenna and compute a cardiogram of the user on the basis of the detected motion, wherein the cardiogram represents the motion of the thorax, induced by the user's heart, with respect to the portable training computer.

2. The portable training computer of claim 1, wherein the at least one processor is configured to detect the proximity of the thorax with respect to the antenna in the first measurement mode and to trigger the second measurement mode during sleep time of the user.

3. The portable training computer of claim 1, further comprising at least one motion sensor, wherein the at least one processor is configured to detect the proximity of the thorax with respect to the antenna in the first measurement mode on the basis of the electric property and motion measurement data, measured by the motion sensor, indicating a gesture where the portable training computer is brought to the proximity of the thorax.

4. The portable training computer of claim 1, further comprising a photoplethysmogram (PPG) sensor, wherein the at least one processor is configured, in the second measurement mode, to detect a blood pulse wave from the cardiogram at a first time instant, to detect the same blood pulse wave in a PPG measured by the PPG sensor at a second time instant, and to compute a pulse transit time of the blood pulse wave on the basis of a difference between the first time instant and the second time instant.

5. The portable training computer of claim 4, wherein the at least one processor is configured to determine the first time instant from a detection time of the blood pulse wave offset by a non-zero-time offset factor.

6. The portable training computer of claim 4, wherein the PPG sensor is further configured to measure the PPG when not in the second measurement mode, and wherein the at least one processor is configured to trigger the second measurement mode and computation of the pulse transit time upon detecting a determined anomaly in the measured PPG.

7. The portable training computer of claim 1, wherein the communication circuitry comprises at least one further antenna configured to a different frequency band than said antenna, wherein the measurement circuitry is coupled to the at least one further antenna and configured to measure an electric property of the at least one further antenna, wherein the measured property of the at least one further antenna comprises at least one of an impedance, a resonance frequency, and a standing wave ratio of the antenna, and wherein the at least one processor is further configured to compute the cardiogram in a third measurement mode on the basis of the measured electric property of the at least one further antenna.

8. The portable training computer of claim 1, wherein the at least one processor is configured, upon determining to enter the second measurement mode, to verify that a position of the antenna is suitable for the cardiogram measurements in the second measurement mode and, upon detecting that the position of the antenna is not suitable for the cardiogram measurements, carry out a function for correcting the position of the antenna.

9. The portable training computer of claim 8, further comprising a user interface, wherein the function comprises outputting an instruction to a user to change the position of the portable training computer.

10. The portable training computer of claim 8, wherein the function comprises electrically modifying directivity of the antenna.

11. The portable training computer of claim 1, wherein the communication circuitry and the antenna are configured to comply with Bluetooth technology.

12. The portable training computer of claim 1, wherein the portable training computer is a wrist computer.

13. The portable training computer of claim 1, wherein the measurement circuitry is configured to measure the antenna impedance only when the communication circuitry is transmitting or receiving the radio frequency signal through the antenna.

14. The portable training computer of claim 1, wherein the communication circuitry is configured to transmit and receive data through the antenna.

15. The portable training computer of claim 1, further comprising a memory configured to store one or more ranges of the electric property that indicate the proximity of the thorax and one or more, different ranges of the electric property that indicate the proximity of the finger or another object, and wherein the at least one processor is configured to distinguish, on the basis of the measured electric property and the stored ranges, whether there is the thorax or the finger or another object in the proximity with the antenna.

16. The portable training computer of claim 15, wherein the at least one processor is configured to trigger the second measurement mode upon distinguishing, on the basis of the measured electric property and the stored ranges, that the thorax is in the proximity with the antenna.

* * * * *